United States Patent [19]
Yue

[11] Patent Number: 5,656,449
[45] Date of Patent: Aug. 12, 1997

[54] NEUTRAL UNSYMMETRICAL CYANINE DYES

[75] Inventor: Stephen T. Yue, Eugene, Oreg.

[73] Assignee: Molecular Probes, Inc., Eugene, Oreg.

[21] Appl. No.: 400,026

[22] Filed: Mar. 6, 1995

[51] Int. Cl.[6] .............................. C12Q 1/04; C12Q 1/00; C12Q 1/32; G01N 33/53
[52] U.S. Cl. ........................... 435/34; 435/4; 435/26; 435/6; 435/968; 435/975; 436/94; 436/800; 536/23.1; 536/26.73; 536/1.11; 536/25.6
[58] Field of Search ..................... 435/34, 4, 26, 435/6, 968, 975; 536/23.1, 26.73, 1.11, 25.6; 436/94, 800

[56] References Cited

U.S. PATENT DOCUMENTS

| | | |
|---|---|---|
| 4,665,024 | 5/1987 | Mansour ............... 435/34 |
| 4,883,867 | 11/1989 | Lee et al. ............... 436/94 |
| 4,957,870 | 9/1990 | Lee et al. ............... 436/94 |
| 5,321,130 | 6/1994 | Yue et al. ............... 435/34 |
| 5,410,030 | 4/1995 | Yue et al. ............... 435/34 |
| 5,436,134 | 7/1995 | Haugland et al. ............... 435/34 |
| 5,534,416 | 7/1996 | Millard et al. ............... 435/4 |

FOREIGN PATENT DOCUMENTS

| | | |
|---|---|---|
| 92/07867 | 4/1993 | WIPO . |
| 94/24213 | 10/1994 | WIPO . |

OTHER PUBLICATIONS

Brooker, et al., J. Am. Chem. Soc. 64, 199 (1942) (month not available).
Hamer, J. Chem. Soc., 799 (1940) (month not available).
Clark, J. Chem. Soc., 507 (1936) (month not available).
Davidson, The Biochemistry of the Nucleic Acids (1976) (month not available).
Wittung et al., Nature 368, 561 (1994) (month not available).
Diwu, et al., Cytometry supp. 7, p. 77, Abstract 426B (1994) (month not available).
Davis, et al., "Clinical Flow Cytometric Analysis", Chapter 8. Diagnostic Flow Cytometry, ed. J. Coon & R. Weinstein, Williams & Wilkins (1991) (month not available).

*Primary Examiner*—Louise Leary
*Attorney, Agent, or Firm*—Allegra J. Helfenstein; Anton E. Skaugset

[57] ABSTRACT

The invention describes the preparation and use of fluorescent stains for nucleic acids derived from neutral unsymmetrical cyanine dyes comprising a substituted benzazolium ring system linked to a methine bridge to a pyridine or quinoline ring system. The fluorescence characteristics of the dyes when complexed with nucleic acids give the dyes utility for the detection of oligonucleotides and nucleic acids in cells, gels and solutions. The dyes have particular utility in the staining of reticulocytes.

25 Claims, No Drawings

NEUTRAL UNSYMMETRICAL CYANINE DYES

FIELD OF THE INVENTION

The invention relates to fluorescent dyes for nucleic acids. In particular, the invention relates to dyes derived from neutral unsymmetrical cyanine dyes. The subject dyes, which form a fluorescent complex in combination with nucleic acids, can be used in analyzing a wide range of biological materials, including living cells.

BACKGROUND

In many fields of life sciences research, including biological, biomedical, genetic, fermentation, aquaculture, agricultural, forensic and environmental research, there is a need to identify nucleic acids, qualitatively and quantitatively, in pure solutions and in biological samples. Such applications require a fast, sensitive, and selective methodology that can detect minute amounts of nucleic acids in a variety of media, whether or not the nucleic acid is contained in cells.

Although certain unsymmetrical cyanine dyes were first described before the genetic role of nucleic acids was established (Brooker, et al., J. AM. CHEM. SOC. 64, 199 (1942)), some unsymmetrical cyanine dyes are now known to be effective fluorescent stains of DNA and RNA. The cationic cyanine dye sold as Thiazole Orange has particular advantages in reticulocyte analysis (U.S. Pat. No. 4,883,867 to Lee, et al. (1989) and No. 4,957,870 to Lee et al. (1990)). Thiazole Orange readily stains many mammalian cells, yet does not effectively stain some eukaryotic cells.

Attachment of various cyclic structures to the pyridinium or quinolinium ring system of selected unsymmetrical cyanine dyes was found to make these nucleic acid stains highly permeant to gels and a wider variety of cell types, including both Gram-positive and Gram-negative bacteria, yeasts, and eukaryotic cells as well as prokaryotic cells, as described in international publication WO 94/24213 (Oct. 27, 1994) corresponding to international application PCT/US94/04127 (Apr. 1, 1993)

Attachment of a cationic side chain at the nitrogen of the pyridinium or quinolininm ring system of the unsymmetrical cyanine dyes, on the other hand, was shown to make the stains relatively impermeant to all cells, except cells, particularly mammalian cells, where cell membrane integrity was destroyed, as described in UNSYMMETRICAL CYANINE DYES WITH CATIONIC SIDE CHAINS (U.S. Pat. No. 5,321,130 to Yue et al. (1994)). A second type of dye, in which a dye monomer is attached at the nitrogen of the quinolinium or pyridininm ring system to form dimeric compounds as described in DIMERS OF UNSYMMETRICAL CYANINE DYES (PCT 92/07867) and DIMERS OF UNSYMMETRICAL CYANINE DYES CONTAINING PYRIDINIUM MOIETIES (U.S. Pat. No. 5,410,030 to Yue, et al., 1995) that is also relatively impermeant to all cells unless the cell membrane has been disrupted. The high sensitivity of nucleic acid detection made possible by these dyes, however, indicates that the affinity, and therefore sensitivity, of the stain corresponds to the increased cationic charge of these unsymmetrical cyanine dyes.

Unlike all of the cyanine dyes described above, the core structure of all of the dyes of the present invention is electrically neutral. Limited examples of these dyes have been previously described (Hamer, J. CHEM. SOC., 799 (1940); Clark, J. CHEM. SOC., 507 (1936)). Although these dyes are useful for the present invention, neither the complex of these dyes with nucleic acids, the use of these cyanine dyes to stain nucleic acids, nor the fluorescence properties of the dyes with or without nucleic acids has been described previously. In particular, the use of the dyes of the present invention to stain the nucleic acids of living cells has not previously been described. Surprisingly, the dyes of the current invention possess unexpected advantages as nucleic acid stains.

First, a formally neutral nucleic acid stain would not be expected to possess a useful affinity for nucleic acid polymers. As described above, the presence of additional cationic charges on already charged cyanine dyes has been shown to lead to higher affinity and sensitivity. Virtually all currently used nucleic acid stains possess at least one permanent positive charge. A formally neutral dye would not be expected to possess sufficient affinity to be a useful nucleic acid stain, because a significant part of the dye-nucleic acid binding energy is expected to be derived from the electrostatic attraction of the cationic dye to the negatively charged nucleic acid polymer. Nevertheless, the instant dyes, for which fluorescence depends on binding to nucleic acid polymers, are sometimes more fluorescent than Thiazole Orange.

In addition, the presence of a positive charge on nucleic acid stains currently used in the art enhances the ability of these dyes to enter cells. Nevertheless, the dyes of the present invention have exhibited utility as live cell stains, particularly when used to stain reticulocytes. As shown in Example 23, the dyes of the invention exhibit uptake rates in live cells comparable to, or faster than, that of Thiazole Orange. In addition, some dyes of the invention are useful in differentiating reticulocytes from other blood cells and blood components.

Further, the dyes of the present invention possess utility as electrophoresis gel stains and in detecting nucleic acids in solution. When viewing a DNA gel using illumination of 254 nm, the limit of detection using Thiazole Orange is 1–2 ng/band. In contrast Dye 510 of the present invention has a detection limit of 180 pg/band, and Dye 798 of the present invention has a detection limit of 350 pg/band (Example 22). These results indicate a utility for detection of nucleic acids that would not be expected in view of the performance of Thiazole Orange.

SUMMARY OF THE INVENTION AND DESCRIPTION OF PREFERRED EMBODIMENTS

The dyes that possess utility for the present invention are virtually non-fluorescent when diluted into aqueous solution. When bound to nucleic acid polymers such as DNA and RNA, however, the resultant dye-nucleic acid complex becomes extremely fluorescent upon illumination. The dyes of the present invention label nucleic acids in a wide variety of samples, particularly in aqueous solutions, electrophoretic gels, and a wide variety of cells, including microorganisms. The dyes of the present invention possess particular utility for staining reticulocytes.

Dye Structure

The dyes that possess utility for the present invention comprise: 1) a first heterocyclic ring system that is a substituted benzazole, 2) a bridging methine or polymethine and 3) a second heterocyclic ring that is a pyridine or quinoline ring system. The first and second ring systems are optionally further substituted by a variety of substituents, as described below.

The dyes of the present invention are described by Formula I:

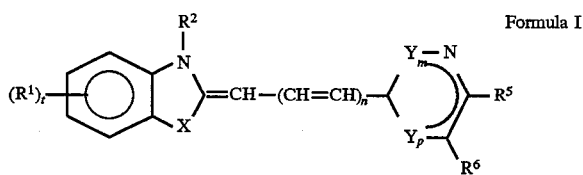

Formula I where the substituted benzazole ring system on the left is linked by a methine or polymethine bridge to the right-hand pyridine or quinoline ring system.

Although $R^1$ on the benzazole ring system is usually H, incorporation of one or more non-hydrogen substituents $R^1$ can be used to fine tune the absorption and emission spectra of the resulting dye. The benzazole ring may contain more than one substituent $R^1$, which may be the same or different (t=1–4). Each $R^1$ is optionally an alkyl group having from 1–6 carbons; or a trifluoromethyl; or a halogen; or an alkoxy having 1–6 carbons. Typically, each compound contains no more than one $R^1$ that is not H. Preferably, $R^1$ is H or alkoxy, more preferably each $R^1$ is H.

The substituent $R^2$ is an alkyl group having 1–6 carbons, preferably methyl or ethyl.

X is one of O, S, Se or $NR^{15}$, where $R^{15}$ is H or an alkyl group having 1–6 carbons. Alternatively, X is $C(CH_3)_2$. Preferably, X is O or S; more preferably X is S.

The two heterocyclic ring systems are linked by 1, 3 or 5 methine (—CH=) groups. When n=0 the dyes are monomethine dyes; when n=1 the dyes are trimethine dyes; when n=2, the dyes are pentamethine dyes. As with similar compounds, the number of methine groups between the heteroaromatic rings influences the spectral properties of the dye. The monomethine dyes of the present invention that are pyridines typically have blue to blue-green fluorescence emission, while quinolines have green to yellow-green fluorescence emission. The trimethine dye analogs are substantially shifted toward red wavelengths, and the pentamethine dyes are shifted even further, often exhibiting infrared fluorescence emission. Preferably n=0 or 1, more preferably n=0.

The second ring system contains a ring fragment Y that is —CH=$CR^4$—, with subscripts p and m equal to 0 or 1, such that p+m=1. For all embodiments, the ring contains a 6-membered pyridine-based heterocycle according to one of these formulations:

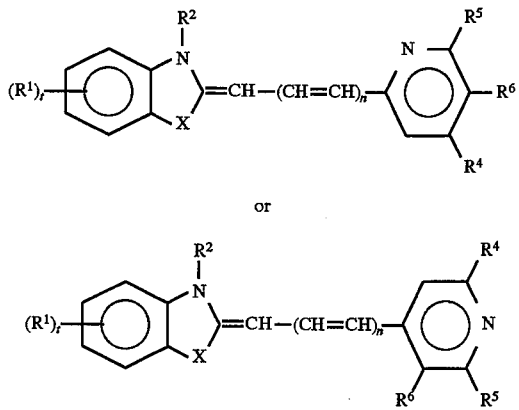

In preferred embodiments of the invention, m=1 and p=0 ("4-pyridines" and "4-quinolines").

The ring substituent $R^4$ is optionally H, or an alkyl, alkoxy, alkylthio, amino, monoalkylamino, dialkylamino, aryl, arylthio, aryloxy, or arylamino, the alkyl portions of which independently contain 1–6 carbons. Alternatively, $R^4$ is a piperazinyl, piperidinyl, pyrrolidinyl, or morpholinyl. The ring substituent $R^4$ is optionally unsubstituted, or the alkyl portions of $R^4$ are optionally further substituted by one or more of hydroxy, carboxy, alkoxy, alkylthio, amino, monoalkylamino, dialkylamino, trialkylammonium, piperidinyl, pyrrolidinyl, piperazinyl or morpholinyl, the alkyl portions of each of which independently contain 1–6 carbon atoms. Where $R^4$ is an aryl, arylthio, aryloxy or arylamino, aryl is defined as phenyl or phenyl substituted one or more times by alkyl, hydroxy, carboxy, alkoxy, amino, alkylamino, or dialkylamino, the alkyl portions of which independently contain 1–6 carbon atoms. Typically $R^4$ is H, alkyl, alkoxy, alkylthio, amino, monoalkylamino or dialkylamino. Where $R^4$ is alkylthio, monoalkylamino or dialkylamino, one or more of the alkyl portions of $R^4$ is typically further substituted by amino, alkylamino, dialkylamino or trialkylammonium. In one embodiment of the invention, $R^4$ is H, methyl or ethyl. In another embodiment of the invention, $R^4$ is substituted or unsubstituted alkoxy, alkylthio, amino, monoalkylamino, or dialkylamino.

The ring substituents $R^5$ and $R^6$ are optionally and independently H, a halogen, an alkyl group having 1–6 carbons, —$OR^8$, —$SR^8$, or —$(NR^8R^9)$, where $R^8$ and $R^9$, which can be the same or different, are independently H, alkyl groups having 1–6 carbons, or $R^8$ and $R^9$ taken in combination are —$(CH_2)_4$— or —$(CH_2)_5$— to give a 5- or 6-membered ring. Alternatively, $R^5$ and $R^6$ taken in combination are —$(CH_2)_v$— where v=3 or 4, forming a fused 5- or 6-membered ring, or $R^5$ and $R^6$, taken in combination form a fused 6-membered aromatic ring. Typically, ring substituents $R^5$ or $R^6$ are independently H, alkyl, —$OR^8$, or taken in combination form a fused 6-membered aromatic ring. Preferably, $R^5$ and $R^6$, taken in combination form a fused 6-membered aromatic ring.

Where $R^5$ and $R^6$ taken in combination form a fused 6-membered aromatic ring, embodiments of this invention are quinoline derivatives according to the formula

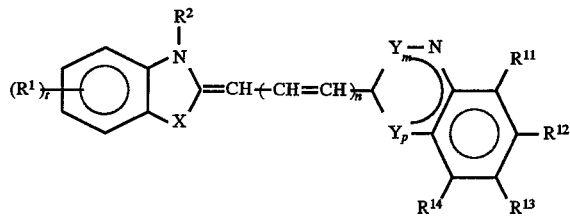

where ring substituents $R^{11}$, $R^{12}$, $R^{13}$, and $R^{14}$ are the same or different, and are independently H, a halogen, or an allkyl group having 1–6 carbons, or —$OR^8$, —$SR^8$, —$(NR^8R^9)$, where $R^8$ and $R^9$ are as defined previously. Preferred embodiment of the invention are quinolines wherein m=1 and p=0 ("4-quinolines"). Preferably $R^{11}$, $R^{12}$, $R^{13}$, and $R^{14}$ are independently H, alkyl, or —$OR^8$, more preferably $R^{11}$, $R^{12}$, $R^{13}$, and $R^{14}$ are each H.

The identity of the $R^4$ substituent has been shown to have a strong effect on the quantum yield of the resulting dyes. In particular, a compound wherein $R^4$ is methyl typically demonstrates a two-fold increase in quantum yield when bound to nucleic acids, relative to analogous compounds where $R^4$ is hydrogen. As examples, see the quantum yield of Dye 523-2 versus Dye 798, and that of Dye 523-1 versus Dye 7100 (See Table 1, and Examples 1, 5 and 7). However, when $R^4$ is a larger alkyl, as for Dye 1268 ($R^4$=n-butyl) the quantum yield of the dye-nucleic acid complex only increases versus Dye 798 when the nucleic acid is DNA.

Similarly, it has been determined that dyes of the present invention for which $R^4$ is a substituted amine, as for Dye 510 (Example 14) display a substantial increase in the quantum yield of the dye-nucleic acid complex, relative to embodiments where $R^4$ is not an amino substituent. Dyes with higher quantum yields permit more sensitive detection of nucleic acids. The preferred dyes of the invention have quantum yields greater than 0.1 when bound to nucleic acids, more preferably greater than 0.2, and yet more preferably greater than 0.4.

Where $R^4$ is a substituted alkylthio, alkylamino or dialkylamino the utility of specific embodiments of the dyes of the present invention in staining live cells and microorganisms is generally dependent on the electronic nature of the $R^4$ substituent. For example, those compounds for which $R^4$ incorporates a cationic charge (tetraalkylammonium) are generally impermeant to living cells, but typically display sufficient selectivity to serve as dead cell stains.

Those embodiments of the invention that incorporate a permanent positive charge as part of the $R^4$ substituent (i.e. quaternary ammonium derivatives) or that incorporate a substituent that may be transiently positively charged as part of $R^4$, $R^5$ or $R^6$ (e.g. a protonated amine) tend to possess an enhanced affinity for nucleic acids, and are preferred embodiments for the detection of nucleic acids in solution and in cells having compromised membranes.

Synthesis

Two basic synthetic strategies are used to prepare the dyes of the present invention.

In the first method, the corresponding N-methylquinolinium cyanine dye is dealkylated (typically demethylated) using a good nucleophile, such as an alkali metal salt of a thiol (e.g. sodium thiophenoxide) in a polar solvent (e.g. DMF, DMSO) (Examples 12–15, 17). Where $R^2$ is ethyl (or a higher alkyl), the N-methyl substituent on the pyridinium or quinolinium ring is removed selectively during dealkylation. Where the $R^2$ substituent is also methyl, two demethylated products may result, but the two products are readily separated by column chromatography. Where the N-substituent is a substituted alkyl, such as 2-methoxyethoxymethyl, other reagents, such as a strong acid, are used to generate the corresponding pyridine or quinoline end product (Example 16).

In the second method, the free base compound is generated by heating a benzazolium salt that contains a good leaving group (chloride, methylthio, etc.) at the 2-position, with a 2- or 4-methyl substituted or unsubstituted quinoline or pyridine in the presence of acetic anhydride as an activator (Examples 1–11).

Method of Use

The method of use of the invention comprises combining a dye of Formula I with a sample that contains or is thought to contain a nucleic acid polymer, incubating the mixture of dye and sample for a time sufficient for the dye to combine with nucleic acid polymers in the sample to form one or more dye-nucleic acid complexes having a detectable fluorescent signal. A detectable fluorescence signal, as used herein, is the occurrence of a fluorescence emission upon illumination of the dye-nucleic acid complex that is capable of being perceived, either by direct observation or instrumentally. The presence or magnitude of the signal is a function of the presence of nucleic acid polymers in the sample. The characteristics of the fluorescent signal, including the presence, location, intensity, excitation and emission spectra, fluorescence polarization, fluorescence lifetime, and other physical properties of the fluorescent signal; are used to detect, differentiate, sort, quantitate, and/or analyze aspects or portions of the sample. The dyes of the invention are optionally used in conjunction with one or more additional reagents, preferably fluorescent reagents, including dyes of the same class having detectably different spectral properties.

Staining Solution

Typically, the subject dye is prepared for use by dissolving the dye in a staining solution, preferably an aqueous or aqueous miscible solution that is compatible with the sample and the intended use. For biological samples, where minimal perturbation of cell morphology or physiology is desired, the staining solution is selected accordingly. For solution assays, the staining solution preferably does not grossly perturb the native conformation of the nucleic acid undergoing evaluation. The staining solution typically has a pH between 6.5 and 8. High concentrations of organic solvents, cations, and oxidizing agents also generally reduce fluorescence, as does the ionic detergent sodium dodecyl sulfate (SDS) at concentrations >0.01%. The dyes have greater stability in buffered solutions than in water alone; and agents that reduce the levels office oxygen radicals, such as β-mercaptoethanol, contribute to the stability of the dyes.

The staining solution is made by dissolving the dye directly in an aqueous solvent such as water, a buffer solution, such as buffered saline (preferably non-phosphate for some viability discrimination applications), a tris (hydroxymethyl)aminomethane (TRIS) buffer (preferably containing EDTA), or a water-miscible organic solvent such as dimethylsulfoxide (DMSO), dimethylformamide (DMF), or a lower alcohol such as methanol or ethanol. The dye is usually preliminarily dissolved in an organic solvent (preferably 100% DMSO) at a concentration of greater than about 1000-times that used in the staining solution, then diluted one or more times with an aqueous solvent such as water or buffer, such that the dye is present in an effective amount. Typically, when the dyes of the present invention are components of a kit for staining nucleic acids, the dyes of the invention are present as DMSO stock solutions having a concentration of 0.5 mM to 10 mM, preferably 1 mM to 5 mM, and the stock solution is present as one or more aliquots of 10 µL to 200 µL, preferably 50 µL to 100 µL.

An effective mount of dye is the mount sufficient to give a detectable fluorescence response in combination with nucleic acids. The dye concentration in the solution must be sufficient both to contact the nucleic acids in the sample and to combine with the nucleic acids in an amount sufficient to give a signal, but too much dye may cause problems with background fluorescence. Typical staining solutions for cellular samples have a dye concentration greater than 0.1 nM and less than 50 µM, more typically greater than 1 nM and less than 10 µM, preferably between 0.5 µM and 5 µM. In general, lower concentrations of dyes are required for eukaryotes than for prokaryotes, and for dyes with higher sensitivity. Staining solutions for electrophoretic gels typically have a dye concentration of greater than 0.1 µM and less than 10 µM, more typically about 0.5–2 µM; the same holds true where the dye is added to the gel (pre-cast) before being combined with nucleic acids. Staining solutions for detection and quantitation of free nucleic acids in solution typically have a concentration of 0.1 µM-2 µM. The optimal concentration and composition of the staining solution is determined by the nature of the sample (including physical, biological, biochemical and physiological properties), the nature of the dye-sample interaction (including the transport rate of the dye to the site of the nucleic acids), and the nature of the analysis being performed, and can be determined according to standard procedures such as those described in examples below.

Sample Types

The dye is combined with a sample that contains or is thought to contain a nucleic acid. The nucleic acid in the sample may be RNA or DNA, or a mixture or a hybrid thereof. Any DNA is optionally single-, double-, triple-, or quadruple-stranded DNA; any RNA is optionally single stranded (ss) or double stranded (ds). The nucleic acid may be a natural polymer (biological in origin) or a synthetic polymer (modified or prepared artificially). The nucleic acid polymer (preferably containing at least 8 bases or base pairs) may be present as nucleic acid fragments, oligonuoleotides, or larger nucleic acid polymers with secondary or tertiary structure. The nucleic acid is optionally present in a condensed phase, such as a chromosome. The nucleic acid polymer optionally contains one or more modified bases or links or contains labels that are non-covalently or covalently attached. For example, the modified base can be a naturally occurring modified base such as ψ (pseudouridine) in tRNA, 5-methylcytosine, 6-methylaminopurine, 6-dimethylaminopurine, 1-methylguanine, 2-methylamino-6-hydroxypurine, 2-dimethylamino-6-hydroxypurine, or other known minor bases (see, e.g. Davidson, THE BIOCHEMISTRY OF THE NUCLEIC ACIDS (1976)) or is synthetically altered to contain an unusual linker such as morpholine derivatized phosphates (AntiVirals, Inc., Corvallis, Oreg.), or peptide nucleic acids such as N-(2-aminoethyl)glycine units (Wittung, et al., Nature 368, 561 (1994)) or contain a simple reactive functional group (<10 carbons) that is an aliphatic amine, carboxylic acid, alcohol, thiol or hydrazine, or contain a fluorescent label or other hapten, such as inosine, bromodeoxyuridine, iododeoxyuridine, biotin, digoxigenin, 2,4-dinitrophenyl, where the label is originally attached on the nucleotide (e.g. "CHROMATIDE" labeled nucleotides, Molecular Probes, Eugene, Oreg.) or on the 3' or 5' end of the polymer (e.g. "ONLY" labeled oligonucleotides, Molecular Probes, Eugene, Oreg.), or ligands non-covalently attached to the nucleic acid. The sensitivity of the dyes for polymers containing primarily modified bases and links may be diminished by interference with the binding mode.

The sample that contains the nucleic acid is optionally a biological structure (i.e. an orgarnism or a discrete unit of an organism), or a solution (including solutions that contain biological structures), or a solid or semi-solid material. Consequently, the nucleic acid used to practice the invention is optionally free in solution, mobilized in or on a solid or semi-solid material, extracted from a biological structure (e.g. from lysed cells, tissues, organisms or organelles), or remains enclosed within a biological structure. In order for the nucleic acids to bind to the dyes, it is necessary that the nucleic acids be in a mostly aqueous environment to contact the dye, even if the nucleic acids are not enclosed in a biological structure.

The biological structure that encloses the nucleic acid is optionally a cell or tissue, for example where the nucleic acid is present in a cell or interstitial space as a prokaryote or eukaryote microorganism, or as a virus, viroid, chromosome or organelle. Alternatively, the biological structure is not enclosed in a tissue or cell, and is present either as a virus or as a microorganism or other cell, or is present as a cellular component removed from its parent cell (e.g. a plasmid or chromosome, or a mitochondrion or nucleus or other organelle). Typically, the biological structure is an organelle, chromosome or cell that is optionally inside a eukaryote cell. The cell that is present inside a eukaryote cell is typically a parasite or other infective agent such as a bacterium, protozoa, mycoplasma or mycobacterium. Where the nucleic acid is contained in a biological structure that is a cell, the cells are viable or dead cells or a mixture thereof, i.e. the integrity of the cell membrane is optionally intact or disrupted by natural (autolytic), mechanical or chemical means or by environmental means such as changes in temperature or pressure. Alternatively, the cells are blebbing or undergoing apoptosis or are in a cycle of growth or cell division.

Cell types for which the dye is an effective nucleic acid stain include cells with or without nuclei, including but not limited to, eukaryotes, such as plant and animal cells (particularly vertebrate cells), including pollen and gamete cells; prokaryotes, particularly bacteria, including both Gram-negative and Gram-positive bacteria; as well as yeast and other fungi, and spores. The dyes are not equally effective in staining all cell types and certain dyes are generally more permeant than others. Live cells are less permeable to the dyes than dead cells, and prokaryotes are less permeable than eukaryote.

In one embodiment of the invention, the dyes of the present invention are used to stain and differentiate blood cells. In a preferred embodiment, the dyes of the present invention are used to differentiate reticulocytes from other components of a blood sample. The differentiation, based on the fluorescence properties of the stained reticulocytes, is optionally used to sort the reticulocytes. Typically the differentiation and optional sorting are performed using a flow cytometer.

The nucleic acids in the sample, both natural and synthetic, may be obtained from a wide variety of sources. The presence of the nucleic acid in the sample may be due to natural biological processes, or the result of a successful or unsuccessful synthesis or experimental methodology, undesirable contamination, or a disease state. The nucleic acid may be endogenous to the natural source or introduced as foreign material, such as by infection, transfection, or therapeutic treatment. Nucleic acids may be present in all, or only part, of a sample, and the presence of nucleic acids may be used to distinguish between individual samples, or to differentiate a portion or region within a single sample, or to identify the sample or characteristics of the sample.

Typically, the sample containing nucleic acids is a cell or is an aqueous or aqueous miscible solution that is obtained directly from a liquid source or as a wash from a solid material (organic or inorganic) or a growth medium in which cells have been introduced for culturing or a buffer solution in which nucleic acids or biological structures have been placed for evaluation. Where the nucleic acids are in cells, the cells are optionally single cells, including microorganisms, or multiple cells associated with other cells in two or three dimensional layers, including multicellular organism, embryos, tissues, biopsies, filaments, biofilms, etc. Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuffs, such as meat, grain, produce, or dairy products.

Where the nucleic acid is present in a solution, the sample solution can vary from one that contains purified or synthetic nucleic acids such as oligonucleotides to crude mixtures such as cell extracts or homogenates or other biological fluids, or dilute solutions from biological, industrial, or environmental sources. In some cases it is desirable to separate the nucleic acids from a mixture of biomolecules or fluids in the solution prior to combination with the dye. Numerous techniques exist for separation and purification of nucleic acids from generally crude mixtures with other proteins or other biological molecules. These include such means as chromatographic techniques and electrophoretic techniques, using a variety of supports or solutions or in a flowing stream..Alternatively, mixtures of nucleic acids may be treated with RNase or DNase so that the polymer that is not degraded in the presence of the nuclease can be discriminated from degradation products using the subject dyes.

Formation of Dye-Nucleic Acid Complex

The sample is combined with the staining solution by any means that facilitates contact between the dye and the nucleic acid. Typically the contact occurs through simple mixing, as in the case where the sample is a solution. A staining solution containing the dye may be added to the nucleic acid solution directly or may contact the nucleic acid solution in a liquid separation medium such as an electrophoretic liquid, sieving matrix or running buffer, or in a sedimentation (e.g. sucrose) or buoyant density gradient (e.g. containing CsCl), or on an inert matrix such as a blot or gel, a testing strip, or any other solid or semi-solid support. Suitable supports also include, but are not limited to, polymeric microparticles (including paramagnetic microparticles), polyacrylamide and agarose gels, nitrocellulose filters, computer chips (such as silicon chips for photolithography), natural and synthetic membranes, liposomes and alginate hydrogels, and glass (including optical filters), and other silica-based and plastic support. The dye is optionally combined with the nucleic acid solution prior to undergoing gel or capillary electrophoresis, gradient centrifugation, or other separation step, during separation, or after the nucleic acids undergo separation. Alternatively, the dye is combined with an inert matrix or solution in a capillary prior to addition of the nucleic acid solution, as in pre-cast gels, capillary electrophoresis or preformed density or sedimentation gradients.

Where the nucleic acids are enclosed in a biological structure, the sample is typically incubated with the dye. While some cyanine dyes have shown an ability to permeate biological structures rapidly and completely upon addition of the dye solution, any other technique that is suitable for transporting the dye into the biological structure is also a valid method of combining the sample with the subject dye. Some cells actively transport the dyes across cell membranes (e.g. endocytosis or ingestion by an organism or other uptake mechanism) regardless of their cell membrane permeability. Suitable artificial means for transporting the dyes (or pre-formed dye-nucleic acid complexes) across cell membranes include, but are not limited to, action of chemical agents such as detergents, enzymes or adenosine triphosphate; receptor- or transport protein-mediated uptake; liposomes or alginate hydrogels; phagocytosis; pore-forming proteins; microinjection; electroporation; hypoosmotic shock; or minimal physical disruption such as scrape loading, patch clamp methods, or bombardment with solid particles coated with or in the presence of the dyes. Preferably, where intact structures are desired, the methods for staining cause minimal disruption of the viability of the cell and integrity of cell or intracellular membranes. Alternatively, the cells are fixed and treated with routine histochemical or cytochemical procedures, particularly where pathogenic organisms are suspected to be present.

The sample is combined with the dye for a time sufficient to form the fluorescent nucleic acid-dye complex, preferably the minimum time required to give a high signal-to-background ratio. Although all of the novel class of dyes are nucleic acid stains, detectable fluorescence within biological structures or in gels requires entry of the dye across the biological membrane or into gels. Optimal staining with a particular dye is dependent upon the physical and chemical nature of the individual sample and the sample medium, as well as the property being assessed. The optimal time is usually the minimum time required for the dye, in the concentration being used, to achieve the highest target-specific signal while avoiding degradation of the sample over time and minimizing all other fluorescent signals due to the dye or other sources. For example, where the dye is chosen to be selective for a particular nucleic acid polymer or type of cell, the optimal time is usually the minimum time required to achieve the highest signal on that polymer or type of cell, with little to no signal from other nucleic acids or other cell types. Over time, undesirable staining may occur as a result of several natural processes: Even very low rates of diffusion may transport small amounts of the sensitive dyes into other cell types. Alternatively, there may be a loss of differentiable staining as cell membranes degrade. Additionally, staining may become indistinct as nucleases degrade nucleic acid polymers in cell free systems.

Preferably, the dye is combined with the sample at a temperature optimal for biological activity of the nucleic acids within the operating parameters of the dyes (usually between 5° C. and 50° C., with reduced stability of the dyes and samples at higher temperatures). For in vitro assays, the dye is typically combined with the sample at about room temperature (23° C.). At room temperature, detectable fluorescence in a solution of nucleic acids is essentially instantaneous depending on the sensitivity of the instrumentation that is used; fluorescence in solutions is generally visible by eye within 5 seconds after the dye is added, and is generally measurable within 2 to 5 minutes, although reaching equilibrium staining may take longer. Where a biological process is underway during in vitro analysis (e.g. in vitro transcription, replication, splicing, or recombination), the rapid labeling that occurs with the subject dyes avoids perturbation of biological system that is being observed. Gel staining at room temperature usually takes from 5 minutes to 2 hours depending on the thickness of the gel and the percentage of agarose or polyacrylamide, as well as the degree of cross-linking. Typically, post-stained minigels stain to equilibrium in 20–30 minutes. For cells and other biological structures, transport of dyes across membranes is required whether the membranes are intact or disrupted. For preferred embodiments, visibly detectable fluorescence is obtained at room temperature within 15–20 minutes of incubation with cells, typically within about 5 minutes, more commonly within 1 minute. Some embodiments give detectable fluorescence inside cells in less than about 2 minutes. Lymphocytes loaded with 5 μM dye solutions give a fluorescence response in less than one minute. The relative permeability of the cell membrane to the dyes is determined empirically, e.g. by comparison with staining profiles or staining patterns of killed cells. The dye with the desired degree of permeability, and a high absorbance and quantum yield when bound to nucleic acids, is selected to be combined with the sample.

Fluorescence of the Dye-Nucleic Acid Complex

The nucleic acid-dye complex formed during the staining of the sample with a dye of the present invention comprises a nucleic acid polymer non-covalently bound to one or more molecules of the dye of Formula I. The combination of dye and nucleic acid results in a fluorescent signal that is significantly enhanced over the fluorescence of the dye alone.

Because the fluorescence for most of this class of dyes in solution is extremely low in the absence of nucleic acids, the absolute degree of enhancement is difficult to determine. The quantum yield of unbound dye is typically <0.01, usually <0.002, and frequently <0.001, which would yield a maximum enhancement of >100x, >500x, and >1000x respectively. Fluorescence of the bound dye is generally about 100-1000 fold greater than that of unbound dye, typically greater than about 300-fold, such that the dyes have a readily detectable increase in quantum yield upon binding to nucleic acids. The molar absorptivity (extinction coefficient) at the longest wavelength absorption peak of the dyes is typically >25,000 $cm^{-1}m^{-1}$ and frequently >30,000 $cm^{-1}m^{-1}$. Dyes with high extinction coefficients at the excitation wavelength are preferred for the highest sensitivity.

TABLE 1

Spectral characteristics of selected dyes of the present invention, when bound to nucleic acids, in comparison with known nucleic acid stains.

| Dye | Excitation/Emmission (nm) (DNA complex) | Quantum Yield (DNA) | Quantum Yield (RNA) |
|---|---|---|---|
| Thiazole Orange* | 510/530 | 0.18 | 0.15 |
| Oxazole Yellow* | 483/504 | 0.31 | 0.54 |
| Dye 4100 | 512/553 | 0.08 | 0.07 |
| Dye 509 | 508/530 | 0.05 | 0.07 |
| Dye 510 | 461/500 | 0.71 | 0.44 |
| Dye 517 | 622/644 | 0.04 | 0.04 |
| Dye 523-1 | 462/521 | 0.25 | 0.29 |
| Dye 523-2 | 493/517 | 0.19 | 0.28 |
| Dye 798 | 491/521 | 0.09 | 0.13 |
| Dye 7100 | 470/533 | 0.11 | 0.09 |
| Dye 1266 | 490/524 | 0.07 | 0.12 |
| Dye 1267 | 475/543 | 0.07 | 0.12 |
| Dye 1268 | 492/517 | 0.25 | 0.24 |
| Dye 7101 | 444/475 | 0.12 | 0.12 |
| Dye 799 | 465/493 | 0.27 | 0.48 |

Quantum yields of selected dyes are detemined bound to double-stranded calf thymus DNA and E. Coli ribosomal RNA. Fluorescence excitation and emission maxima on double-stranded DNA are indicated; units are nm.
*Lee et al. U. S. Pat. No. : 4,883,867 (1989).

The presence, location, and distribution of the nucleic acid is detected via the detectable fluorescent signal of the dye-nucleic acid complex, specifically by analyzing or detecting the spectral properties dye-nucleic acid complex. Spectral properties include any parameter that may be used to characterize the excitation or emission of the dye-nucleic acid complex including absorption and emission wavelengths, fluorescence polarization, fluorescence lifetime, fluorescence intensity, quantum yield, and fluorescence enhancement. Typically the spectral properties of excitation and emission wavelength are used to detect the dye-nucleic acid complex. The wavelengths of the excitation and emission bands of the dyes vary with dye composition to encompass a wide range of illumination and detection bands. This allows the selection of individual dyes for use with a specific excitation source or detection filter. In particular, complexes formed with dyes having a monomethine bridge (n=0) generally match their longest wavelength excitation band with the commonly used argon laser (488 nm) or HeCd laser (442 nm); whereas those with dyes with a trimethine bridge (n=1) primarily tend to match long wavelength excitation sources such as green HeNe laser (543 nm), the orange HeNe laser (594 nm), the red HeNe laser (633 nm), mercury arc (546 nm), or the Kr laser (568 or 647 nm); and complexes formed with dyes having a pentamethine bridge (n=2) primarily match very long excitation sources such as laser diodes or light emitting diodes (LEDs). In addition to the primary excitation peak in the visible range, the dye-nucleic acid complexes of the invention have a secondary absorption peak that permits excitation with UV illumination. Dyes with n=1 and n=2 form nucleic acid complexes that permit excitation beyond 600 nm.

Typically, the sample is excited by a light source capable of producing light at or near the wavelength of maximum absorption of the fluorescent complex, such as an ultraviolet or visible wavelength emission lamp, an arc lamp, a laser, or even sunlight or ordinary roomlight. Preferably the sample is excited at a wavelength within 20 nm of the maximum absorption of the fluorescent complex. Although excitation by a source more appropriate to the maximum absorption band of the nucleic acid-dye complex results in higher sensitivity, the equipment commonly available for excitation of samples can be used to excite the dyes of the present invention.

The fluorescence of the complex is detected qualitatively or quantitatively by detection of the resultant light emission at a wavelength of greater than about 450 nm, preferably greater than about 480 nm, more preferably at greater than about 500 nm. Dyes having a quinoline ring system usually absorb and emit at longer wavelength maxima than similarly substituted dyes having a pyridine ring system. The emission is detected by means that include visual inspection, CCD cameras, video cameras, photographic film, or the use of current instrumentation such as laser scanning devices, fluorometers, photodiodes, quantum counters, plate readers, epifluorescence microscopes, scanning microscopes, confocal microscopes, flow cytometers, capillary electrophoresis detectors, or by other means for amplifying the signal such as a photomultiplier tube. Many such instruments are capable of utilizing the fluorescent signal to sort and quantitate cells or quantitate the nucleic acids. Dyes can be selected to have emission bands that match commercially available filter sets such as that for fluorescein or for detecting multiple fluorophores with several excitation and emission bands.

Use of Complex

Once the dye-nucleic acid complex is formed, its presence is detected and used as an indicator of the presence, location, or type of nucleic acids in the sample, or as a basis for sorting cells, or as a key to characterizing the sample or cells in the sample. Such characterization may be enhanced by the use of additional reagents, including fluorescent reagents. The nucleic acid concentration in a sample is quantified by comparison with previously determined relationships between the fluorescence of the nucleic acid-dye complex and concentration of nucleic acids in the sample.

In one aspect of the invention, the dye-nucleic acid complex is used as a means for detecting the presence or location of nucleic acids in a sample, where the sample is stained with the dye as described above, and the presence and location of a fluorescent signal indicates the presence of nucleic acids at the corresponding location. The fluorescent signal is detected by eye or by the instrumentation described above. The general presence or location of nucleic acids is typically detected in a static liquid solution or suspension, or in a flowing stream such as a flow cytometer, or in a centrifugation gradient, or in a separation medium, such as a gel or electrophoretic fluid, or when leaving the separation medium. For example, nucleic acid polymers are detected with high sensitivity in a wide variety of solutions and separation media, including electrophoretic gels such as acrylamide and agarose gels, both denaturing and non-denaturing, and in other electrophoretic fluids, such as in capillary electrophoresis. Attachment of covalent labels to the polymers used to form the dye-nucleic acid complex does not prevent subsequent formation of the fluorescent complex.

Alternatively, the presence or location of nucleic acids, stained as above, is used to indicate the presence or location of organisms, cells, or organelles containing the nucleic acids, where the presence or location of the fluorescent signal corresponds to the presence or location of the biological structure (e.g. stained cells or organcelles). Infective agents such as bacteria, mycoplasma, mycobaeteria, viruses and parasitic microorganisms, as well as other cells, can be stained and detected inside of eukaryote cells, although the fluorescent signal generated by an individual virus particle is below the resolution level of standard detection instrumentation. In a further embodiment of the invention the fluorescent signal resulting from formation of the dye-nucleic acid complex is used as a basis for sorting cells, for example sorting stained cells from unstained cells or sorting cells with one set of spectral properties from cells with another set of spectral properties, in particular, the sorting of reticulocytes.

In addition to detection of the presence or location of nucleic acids as well as their enclosing structures, the staining profile that results from the formation of the dye-nucleic acid complex is indicative of one or more characteristics of the sample. By staining profile is meant the shape, location, distribution, spectral properties of the profile of fluorescent signals resulting from excitation of the fluorescent dye-nucleic acid complexes. The sample is characterized simply by staining the sample and detecting the staining profile that is indicative of a characteristic of the sample. More effective characterization is achieved by utilizing a dye that is selective for a certain characteristic of the sample being evaluated or by utilizing an additional reagent (as described below), where the additional reagent is selective for the same characteristic to a greater or lesser extent or where the additional reagent is selective for a different characteristic of the same sample.

In a further embodiment of the invention, the shape and distribution of the staining profile of dye-nucleic acid complexes is indicative of the type of cell or biological structure that contains the stained nucleic acids. Cells may be discriminated by eye based on the visual fluorescent signal or be discriminated by instrumentation as described above, based on the spectral properties or localization of the fluorescent signal. Typically the staining profile used to characterize the sample is indicative of the presence, shape, or location of organelles or of cells, where the cells are located in a biological fluid, in a tissue, or in other cells. In one aspect, the staining profile is used to characterize different blood cells, including but not limited to reticulocytes.

In another embodiment of the invention, the staining profile results from the formation of the dye-nucleic acid complex in an electrophoretic gel, or sedimentation or centrifugation gradient. In addition to indicating the presence of nucleic acids in the gel, the staining profile is indicative of one or more characteristics of the nucleic acid solution applied to the gel. The amber of bands and/or the intensity of the signal per band of the staining profile, for example, is indicative of the purity or homogeneity of the nucleic acid solution. Band tightness and degree of smearing is indicative of the integrity of the nucleic acid polymers in the solution. The size, conformation, and composition of the polymers, are indicated by the relative mobility of the polymer through the gel, which can be used to detect changes caused by interaction of analytes with the nucleic acid polymer such as protein binding or enzymatic activity. Preferred embodiments of the dyes have low intrinsic fluorescence so there is no need to destain gels to remove free dye.

Additional Reagents

The dyes of the invention can be used in conjunction with one or more additional reagents that are separately detectable. The additional reagents are separately detectable if they are used separately, e.g. used to stain different aliquots of the same sample or if they stain different parts or components of a sample, regardless of whether the signal of the additional reagents is detectably different from the fluorescent signal of the dye-nucleic acid complex. Alternatively, the dye of the invention is selected to give a detectable response that is different from that of other reagents desired to be used in combination with the subject dyes. Preferably the additional reagent or reagents are fluorescent and have different spectral properties from those of the dye-nucleic acid complex. For example, dyes that form complexes that permit excitation beyond 600 nm can be used in combination with commonly used fluorescent antibodies such as those labelled with fluorescein isothiocyanate or phycoerythrin. Any fluorescence detection system (including visual inspection) can be used to detect differences in spectral properties between dyes, with differing levels of sensitivity. Such differences include, but are not limited to, a difference in excitation maxima, a difference in emission maxima, a difference in fluorescence lifetimes, a difference in fluorescence emission intensity at the same excitation wavelength or at a different wavelength, a difference in absorptivity, a difference in fluorescence polarization, a difference in fluorescence enhancement in combination with target materials, or combinations thereof. The detectably different dye is optionally one of the dyes of the invention having different spectral properties and different selectivity. In one aspect of the invention, the dye-nucleic acid complex and the additional detection reagents have the same or overlapping excitation spectra, but possess visibly different emission spectra, generally having emission maxima separated by >10 nm, preferably >20 nm, more preferably >50 nm. Simultaneous excitation of all fluorescent reagents may require excitation of the sample at a wavelength that is suboptimal for each reagent individually, but optimal for the combination of reagents. Alternatively, the additional reagent(s) can be simultaneously or sequentially excited at a wavelength that is different from that used to excite the subject dye-nucleic acid complex. In yet another alternative, one or more additional reagents are used to quench or partially quench the fluorescence of the dye-nucleic acid complex, such as by adding a second reagent to improve the selectivity for a particular nucleic acid or the AT/GC selectivity.

The additional dyes are optionally used to differentiate cells or cell-free samples containing nucleic acids according to size, shape, metabolic state, physiological condition, genotype, or other biological parameters or combinations thereof. The additional reagent is optionally selective for a particular characteristic of the sample for use in conjunction with a non-selective reagent for the same characteristic, or is selective for one characteristic of the sample for use in conjunction with a reagent that is selective for another characteristic of the invention. In one aspect of the invention, the additional dye or dyes are metabolized intracellularly to give a fluorescent product inside certain cells but not inside other cells, so that the fluorescence response of the cyanine dye of the invention predominates only where such metabolic process is not taking place. Alternatively, the additional dye or dyes are specific for some external component of the cell such as cell surface proteins or receptors, e.g. fluorescent lectins or antibodies. In yet another aspect of the invention, the additional dye or dyes actively or passively cross the cell membrane and are used to indicate the integrity or functioning of the cell membrane (e.g. calcein AM or BCECF AM). In another aspect of the invention, the additional reagent is an organelle stain, i.e. a stain that is selective for a particular organelle, for example the additional reagent(s) may be selected for potential sensitive uptake into the mitochondria (e.g. rhodamine 123 or tetramethylrosamine) or for uptake due to pH gradient in an organelle of a live cell (e.g. Diwu, et al., CYTOMETRY supp. 7, p 77, Abstract 426B (1994)).

The additional dyes are added to the sample being analyzed to be present in an effective amount, with the optimal concentration of dye determined by standard procedures generally known in the art. Each dye is optionally prepared in a separate solution or combined in one solution, depending on the intended use. After illumination of the dyed cells at a suitable wavelength, as above, the cells are analyzed according to their fluorescence response to the illumination. In addition, the differential fluorescence response can be used as a basis for sorting the cells or nucleic acids for further analysis or experimentation. For example, all cells that "survive" a certain procedure are sorted, or all cells of a certain type in a sample are sorted. The cells can be sorted manually or using an automated technique such as flow cytometry, according to the procedures known in the art, such as in U.S. Pat. No. 4,665,024 to Mansour, et al. (1987).

The examples below are given so as to illustrate the practice of this invention. They are not intended to limit or define the entire scope of this invention.

EXAMPLES

Example 1. Preparation of Dye 798:
The following compound is prepared:

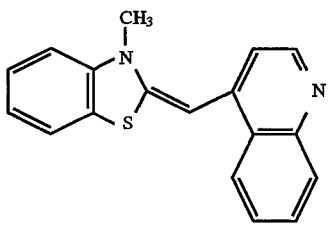

A mixture of 0.37 g (1 mmol) of 3-methyl-2-methylthiobenzothiazolium tosylate, 0.143 g (1 mmol) of lepidine and 0.1 g (1 mmol) of acetic anhydride is heated in 1.5 mL of DMF at 100°–110° C. for four hours. The reaction mixture is cooled to room temperature and 10 mL of ethyl acetate is added. The product, 4-(2,3-dihydro-3-methyl-(benzo-1,3-thiazol-2-yl)-methylidine)-quinolinium tosylate, is collected by filtration.

Example 2. Preparation of Dye 799:
The following compound is prepared:

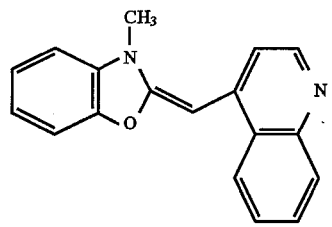

The compound is prepared exactly analogously to Dye 798 (Example 1), excepting that 3-methyl-2-methylthiobenzoxazolium tosylate is used in place of 3-methyl-2-methylthiobenzothiazolium tosylate.

Example 3. Preparation of Dye 1200:
The following compound is prepared:

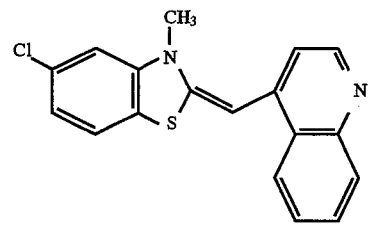

The compound is prepared exactly analogously to Dye 798 (Example 1 ), excepting that 5-chloro-3-methyl-2-methylthiobenzothiazolium tosylate is used in place of 3-methyl-2-methylthiobenzothiazolium tosylate.

Example 4. Preparation of Dye 7101:
The following compound is prepared:

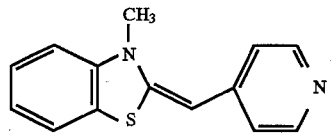

The compound is prepared exactly analogously to Dye 798 (Example 1), excepting that 4-picoline is used in place of lepidine.

Example 5. Preparation of Dye 7100:
The following compound is prepared:

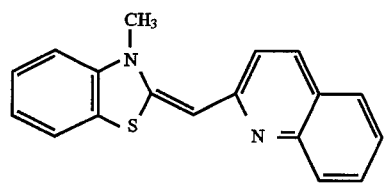

The compound is prepared exactly analogously to Dye 798 (Example 1), excepting that 6-methoxyquinaldine is used in place of lepidine.

Example 6. Preparation of Dye 1267:

The following compound is prepared:

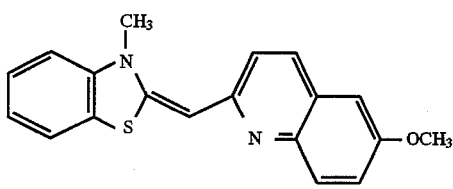

The compound is prepared exactly analogously to Dye 798 (Example 1), excepting that 6-methoxyquinaldine is used in place of lepidine. The crude product is purified by column chromatography on silica gel, using 1:4 ethyl acetate/hexanes as eluant.

Example 7. Preparation of Dyes 523-1 and 523-2:

The following compounds are prepared:

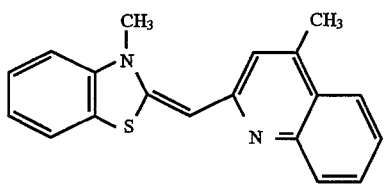
Dye 523-1

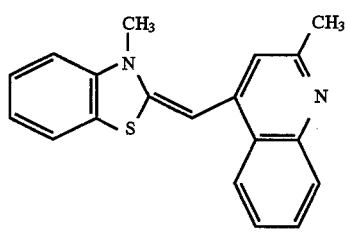
Dye 523-2

The compounds are prepared exactly analogously to Dye 798 (Example 1), excepting that 2,4-dimethylquinoline is used in place of lepidine. The resulting mixture of isomers is purified by column chromatography on silica gel, using 4:4:1 ethyl acetate/chloroform/methanol as eluant, and differentiated using Nuclear Magnetic Resonance Spectroscopy.

Example 8. Preparation of Dye 1100:

The following compound is prepared:

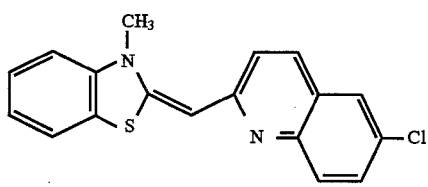

The compound is prepared exactly analogously to Dye 798 (Example 1), excepting that 6-chloroquinaldine is used in place of lepidine.

Example 9. Preparation of Dye 9900:

The following compound is prepared:

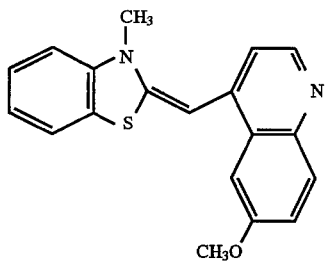

The compound is prepared exactly analogously to Dye 798 (Example 1), excepting that 6-methoxy-4-methylquinoline is used in place of lepidine.

Example 10. Preparation of Dye 8900:

The following compound is prepared:

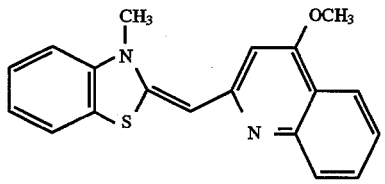

The compound is prepared exactly analogously to Dye 798 (Example 1), excepting that 4-methoxyquinaldine is used in place of lepidine.

Example 11. Preparation of Dye 5700:

The following compound is prepared:

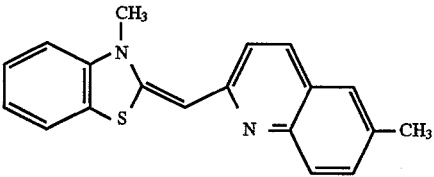

The compound is prepared exactly analogously to Dye 798 (Example 1), excepting that 2,6-dimethylquinoline is used in place of lepidine.

Example 12. Preparation of Dye 4100:

The following compound is prepared:

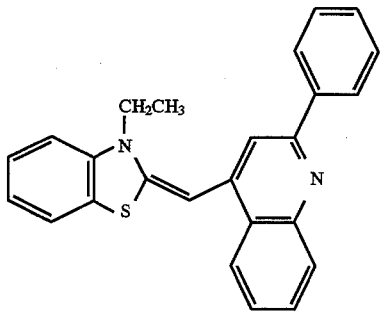

To 0.524 g (3 mmol) of 1,4-dimethyl-1,2-dihydro-2-quinolone in 25 mL of THF at −78° C. under nitrogen is added 2 equivalents of phenyl lithium. The reaction mixture is stirred at −78° C. for one hour. To the cold solution is added four equivalents of acetic acid, the cooling bath is removed, and the reaction mixture is stirred for an additional hour at room temperature. The volatile components are removed under reduced pressure, and the resulting residue is dried in vacuo at 40° C. for 2 hours. The resulting solid is suspended in 20 mL of methylene chloride, and 1.1 g (3 mmol) of 3-ethyl-2-ethylthiobenzothiazolium iodide is added followed by 0.42 mL of triethylamine. The reaction is stirred for 30 minutes, and the volatile components are removed under reduced pressure. The resulting residue is dissolved in a mixture of 30 mL DMF/10 mL MeOH and added dropwise to a solution containing 7 g of sodium iodide in 240 mL of water. The erode iodide salt of the product is recovered and recrystallized to yield 0.64 g of the desired intermediate 4-(2,3-dihydro-3-ethyl(benzo-1,3-thiazol-2-yl)-methylidene)(1-methyl-2-phenylquinolinium iodide. This iodide (0.2 g) is demethylated by healing with 2 equivalents of sodium thiophenoxide in 3 mL of DMF (150° C. for one hour). The crude quinoline is purified on a silica gel column eluting with a 6:6:1 mixture of ethyl acetate/chloroform/methanol.

Example 13. Preparation of Dye 509:
The following compound is prepared:

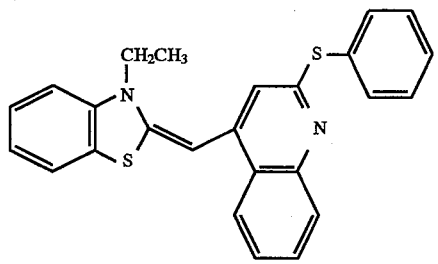

The starting material 2-chloro-4-(2,3-dihydro-3-ethyl-(benzo-1,3-thiazol-2-yl)-methylidene)-1-methylquinolinium chloride is prepared by heating the commercially available 2-chloro-3-methylquinoline with an excess of methyl iodide in a sealed robe at 120° C. for one hour. At the end of the reaction, ethyl acetate is added and the precipitate is filtered to isolate the quinolinium iodide. This intermediate compound is then stirred with 3-ethyl-2-methylthiobenzothiazolium tosylate in methylene chloride in the presence of one equivalent of triethylamine to yield the desired starting material.

A solution of the 4-(2,3 -dihydro-3 -ethyl-(benzo- 1,3-thiazol-2-yl)-methylidene)-2-chloro-1-methylquinolinium chloride (0.965 g, 2.65 mmol) and three equivalents of sodium thiophenoxide is heated at 115° C. The crude product is purified by column chromatography on silica gel using 8:1 chloroform/ethyl acetate as eluant.

Example 14. Preparation of Dye 510:
The following compound is prepared:

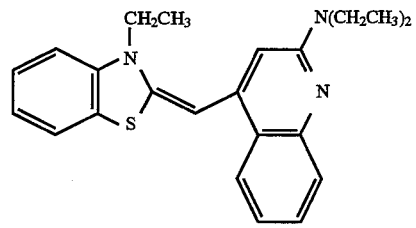

The starting material, 4-(2,3-dihydro-3-ethyl-(benzo-1,3-thiazol-2-yl)-methylidene)-2-diethylamino-1-methylquinolinium iodide is prepared by heating 4-(2,3-dihydro-3-ethyl-(benzo-1,3-thiazol-2-yl)-methylidene)-2-chloro-1-methylquinolinium chloride (Example 8) at 55° C. with diethylamine in 1.5 mL of DMF overnight. The intermediate is isolated by a simple filtration.

The intermediate above (0.21 g) is heated with 2 equivalents of sodium thiophenoxide in 7 mL of DMF at 115° C. for seven hours. The resulting crude product is purified by column chromatography on silica gel using 4:4:1 ethyl acetate/chloroform/methanol as eluant.

Example 15. Preparation of Dye 1266:
The following compound is prepared:

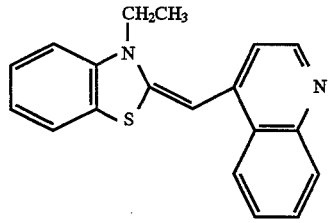

The product is obtained by demethylating 4-(2,3-dihydro-3-ethyl-(benzo-1,3-thiazol-2-yl)-methylidene)-I-methylquinolimum iodide using 3 equivalents of sodium thiophenoxide in DMF at about 120° C. The resulting crude product is purified by column chromatography on silica gel using 2:1 ethyl acetate/hexanes as eluant.

Example 16. Preparation of Dye 517:
The following compound is prepared:

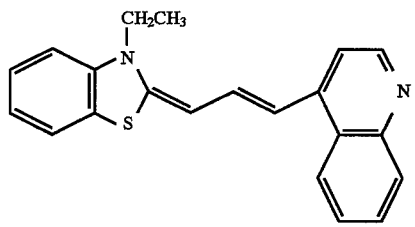

The desired product is obtained from the hydrolysis of 4-(2,3 -dihydro-3-methyl-(benzo-1,3-thiazol-2-yl)-propenylidene)-1-(2-methoxyethoxymethyl) -quinolinium iodide (0.35 g) using a 48% aqueous solution of MeOH/HBr (35 mL/17.5 mL) by heating the reaction mixture at reflux for eight hours. All the volatile compounds are removed under reduced pressure and the residue is suspended in 30 mL of water. The aqueous solution is made basic using 10% NaOH, and extracted with chloroform. The crude product is purified by column chromatography on silica gel using 1:4 ethyl acetate/chloroform as eluant.

Example 17. Preparation of Dye 1268:
The following compound is prepared:

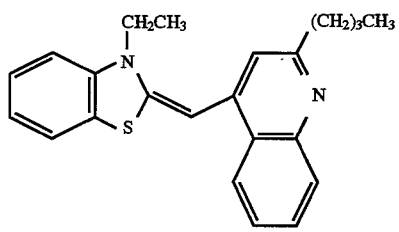

To 1,4-dimethyl-1,2-dihydro-2-quinolone in THF at −78° C. under nitrogen is added 1.2 equivalents of n-butyl lithium. The reaction is stirred at −78° C. for 15 minutes, and then the temperature is raised to 0° C. for another minutes, at which time the reaction is quenched with acetic acid and all volatile components are removed under reduced pressure. The resulting residue is dissolved in methylene chloride and 1 equivalent of 3-ethyl-2-ethylthiobenzothiazolium tosylate is added, followed by 2 equivalents of triethylamine. The reaction mixture is stirred for an additional 20 minutes at room temperature and the crude product is isolated as the iodide salt after a salt exchange.

This intermediate iodide compound, 2-butyl-4-(2,3-dihydro-3-ethyl-(benzo-1,3-thiazol-2-yl)-methylidene)-1-methylquinolinium iodide, is then demethylated with 3 equivalents of sodium thiophenoxide in DMF at 120° C. to give the desired product.

Example 18: Flow cytometric analysis of human peripheral blood reticulocytes using Dye 798:

Human blood is collected by venipuncture into a sterile container containing $K_3$EDTA. One mL of phosphate-buffered saline (PBS), pH 7.4, is added to a 5 mL polystyrene tube. One mL of 150 nM Dye 798 in PBS is added to another 5 mL tube. Five µL of whole blood is added to each tube and mixed. The tubes are incubated for 30 minutes at room temperature. Both samples are analyzed by flow cytometry using the unstained erythrocytes to establish a 488 nm-excited autofluorescence limit in FL1. Counts above this threshold are counted as reticulocytes. Data analysis and quality control procedures are as described in the literature (e.g. Davis et al. "Clinical Flow Cytometric Analysis", Chapter 8, DIAGNOSTIC FLOW CYTOMETRY, ed. J. Coon & R. Weinstein, Williams & Wilkins, 1991.)

Example 19: Detection of vegetative Bacillus cereus in heat-treated nutrient broth:

Fifty mL of nutrient broth are added to each of five 100 mL serum bottles, and the bottles are sterilized by autoclaving at 250° C. for 30 minutes. Upon cooling, $1 \times 10^6$ Bacillus cereus spores are added to each serum bottle containing sterile nutrient broth. The spore suspensions are distributed into sterile glass tubes with standard bacteriological closures. In duplicate, the tubes are subjected to immersion is a boiling water bath for periods ranging between 5 and 80 minutes. After cooling, the tubes are incubated at 35° C. for 3 and 6 hours. After this time, 1 mL samples are distributed into 1.5 mL polypropylene microfuge tubes and the tubes are centrifuged for 10 minutes at 10,000 rpm. The supernate in each tube is removed, and the residual pellet is resuspended in 100 µL of 0.85% NaCl containing 5 µM Dye 1266. The mixture is incubated for 15 minutes at room temperature, after which a 10 µL aliquot is removed from each sample, and trapped between a slide and coverslip. Vegetative bacteria are observed in an epi-fluorescence microscope equipped with a 60X 1.4 NA objective lens and standard long-pass fluorescein filter set (485 nm excitation/520 nm emission).

Example 20: Discrimination of plasma membrane-compromised 3T3 fibroblasts using Dye 4100:

NIH 3T3 fibroblasts are grown to 75% confluency on 18 mm² glass coverslips under standard tissue culture conditions. Coverslips of 3T3 cells are exposed to 0.0001% to 0.1% saponin in HEPES-buffered complete saline solution (HBSS) for 10 minutes at room temperature and subsequently rinsed into HBSS containing 0.1 or 1.0 µM Dye 4100. After incubation for 5 minutes, coverslips are washed with HBSS and mounted on glass microscope slides using glass coverslips as spacers to avoid crushing the cells. The cell fluorescence is observed in the epi-fluorescence microscope using a 40X 0.85 NA objective lens and a standard rhodamine long-pass filter set (546 nm excitation/580 nm emission). Cells with compromised plasma membranes stain brightly while untreated 3T3 cells are virtually unstained.

Example 21: Viability determination of cultured Saccharomyces cerevisiae:

A culture of Saccharomyces cerevisiae is grown in 75 mL of yeast extract-peptone-dextrose (YPD) broth for 2 weeks at 30° C., shaking at 200 rpm in a capped 250 mL Erlenmeyer flask. A 2 mL sample is taken aseptically each day. One mL of this sample is serially diluted in sterile 2% glucose solution and 0.1 mL plated on YPD agar in standard r 100 mm petri dishes. Yeast numbers in the dilution samples having visible turbidity are quantified using a Petroff-Hauser counting chamber. The other 1 mL of the sample is centrifuged in a microcentrifuge at 5,000 rpm for 5 minutes, and resuspended in 100 µL of 1 µM Dye 509 in 2% sterile dextrose solution. After incubation for 15 minutes with the dye, the sample is diluted to 3 mL and the 490 nm-excited 520 m fluorescence is measured relative to a series of standard fluorescein solutions spanning a 10,000-fold range in fluorescence. The increase in the proportion of dead Saccharomyces cells is reflected by an increase in fluorescence at 520 nm when compared with the viable cell plate counts after correction for the total cell numbers derived from the Petroff-Hauser counts.

Example 22. Staining of nucleic acids in electrophoresis gels:

Two separate 1% agarose/TBE (89 mM tris-borate, 2 mM EDTA) minigels are loaded with Lambda DNA/Hind III fragments in a 3-fold serial dilution series of 1 µg, 333 ng, 111 ng, 37.0 ng, 12.4 ng 4.1 ng, 1.4ng. 0.5 ng, 0.2 ng, and 0.05 ng per lane. After the gels are subjected to electrophoresis, the gels are stained with either Dye 510 or Dye 798, as a 1 µM solution in 1XTBE for 30 minutes.

After staining, each gel is illuminated at 254 nm using an epi-illuminator. Gels are photographed with POLAROID 667 black and white print film, Dye 798 stains the gel with a detection limit of 350 pg/band, while Dye 510 stains the gel with a detection limit of 180 pg/band. Both dyes stain the DNA-containing bands with a blue-green fluorescence, however the gel stained with Dye 798 has no observable background staining.

Example 23. Determination of the rate of dye uptake in live cells:

Dye uptake data were acquired using rat basophilic leukemia (RBL) cells. A suspension of RBL cells at a concentration of $1 \times 10^6$ cells/mL is prepared in room-temperature HEPES-buffered Tyrode's buffer containing 0.1% bovine serum albumin. Three µL of a 1 mM dye solution (in DMSO) is added at T=0 to an acrylic, 1 cm pathlength fluorescence cuvette containing 3 mL of the previously prepared RBL cell suspension. The suspension is then stirred continuously with a Teflon-coated magnetic stir bar. The samples are excited at 490 nm, and the fluorescence emission of the suspension at 520 nm is measured at 200 msec intervals for at least 5 minutes. The $T_{1/2}$ value represents the time, in seconds, required for the fluorescence of the suspension to reach an intensity half-way between basal fluorescence level and peak fluorescence (±~2 sec). The data for selected dyes of the invention are presented below.

| Dye | $T_{1/2}$ for cell loading |
| --- | --- |
| Thiazole Orange | 9 sec |
| Dye 798 | 3 sec |
| Dye 799 | 2 sec |
| Dye 523-1 | 41 sec |

-continued

| Dye | $T_{1/2}$ for cell loading |
|---|---|
| Dye 523-2 | 1 sec |
| Dye 1266 | 2 sec |
| Dye 1268 | 3 sec |
| Dye 7101 | 7 sec |

Although the dyes of the invention possess a core structure that is formally electrically neutral, they are taken up by living cells at a rate comparable to that of Thiazole Orange, which is cationically charged.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula

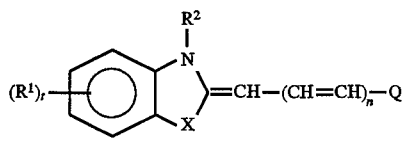

wherein each $R^1$ is independently H; or an alkyl group having from 1–6 carbons; an alkoxy group having from 1–6 carbons; trifluoromethyl; or a halogen; and t=1–4;

$R^2$ is an alkyl group having 1–6 carbons;

X is O, S, Se or $C(CH_3)_2$;

n=0, 1 or 2;

Q has the formula Q1 or Q2

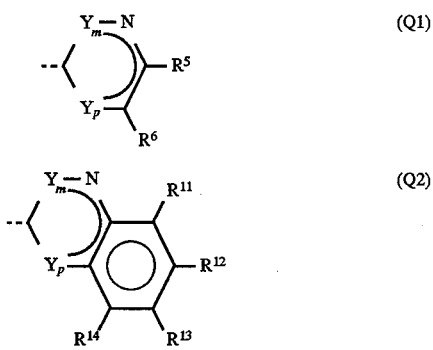

wherein

Y is —CH=CR$^4$—;

p and m=0 or 1, such that p+m=1;

$R^4$ is optionally H, alkyl, alkoxy, alkylthio, amino, monoalkylamino, dialkylamino, arylthio, aryloxy, arylamino, piperazinyl, piperidinyl, pyrrolidinyl or morpholinyl; where each alkyl group independently contains 1–6 carbons and is optionally further substituted one or more times by hydroxy, carboxy, alkoxy, alkylthio, amino, monoalkylamino, dialkylamino, trialkylammonium, piperazinyl, piperidinyl, pyrrolidinyl or morpholinyl, the alkyl portions of which contain 1–6 carbon atoms; or $R^4$ is aryl or aryl substituted one or more times by alkyl, hydroxy, alkoxy, amino, alkylamino, or dialkylamino, the alkyl portions of which contain 1–6 carbon atoms;

$R^5$ and $R^6$, which may be the same or different, are independently H; or a halogen; or an alkyl having 1–6 carbons; or —OR$^8$, —SR$^8$, —(NR$^8$R$^9$); where $R^8$ and $R^9$, which can be the same or different, are independently H; or alkyl groups having 1–6 carbons; or $R^8$ and $R^9$ taken in combination are —(CH$_2$)$_4$— or —(CH$_2$)$_5$— to give a 5 or 6 membered ring;

or $R^5$ and $R^6$, taken in combination are —(CH$_2$)$_v$13 where v=3 or 4, or $R^5$ and $R^6$ form a fused aromatic ring according to formula Q2; and $R^{11}$, $R^{12}$, $R^{13}$, and $R^{14}$, which may be the same or different, are independently H; or a halogen; or an alkyl having 1–6 carbons; or —OH, —OR$^8$, —SR$^8$, or —(NR$^8$R$^9$);

such that where X is S, $R^4$ is not H.

2. A compound, as claimed in claim 1, wherein X is O or S.

3. A compound, as claimed in claim 1, wherein each $R^1$ is H, and $R^2$ is methyl or ethyl.

4. A compound, as claimed in claim 3, wherein X is O and $R^4$ is H.

5. A compound, as claimed in claim 1, wherein n=0 or 1.

6. A compound, as claimed in claim 1, wherein $R^4$ is H, methyl or ethyl.

7. A compound, as claimed in claim 1, wherein $R^4$ is a substituted or unsubstituted alkylthio, alkylamino or dialkylamino.

8. A fluorescent complex comprising a nucleic acid polymer non-covalently bound to one or more dye molecules of the formula

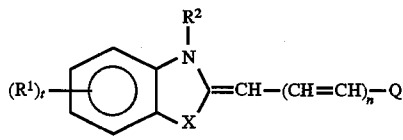

wherein each $R^1$ is independently H; or an alkyl group having from 1–6 carbons; an alkoxy group having from 1–6 carbons; or a trifluoromethyl; or a halogen; and t=1–4;

$R^2$ is an alkyl group having 1–6 carbons;

X is O, S, Se or $C(CH_3)_2$;

n=0, 1 or 2;

Q has the formula Q1 or Q2

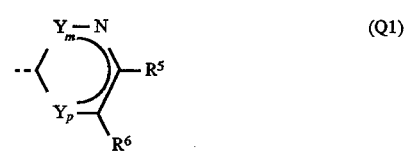

wherein

Y is —CH=CR$^4$—;

p and m=0 or 1, such that p+m=1;

$R^4$ is optionally H, alkyl, alkoxy, alkylthio, amino, monoalkylamino, dialkylamino, arylthio, aryloxy, arylamino, piperazinyl, piperidinyl, pyrrolidinyl or morpholinyl; where each alkyl group independently contains 1–6 carbons and is optionally further substituted one or more times by hydroxy, carboxy, alkoxy, alkylthio, amino, monoalkylamino, dialkylamino, trialkylammonium, piperazinyl, piperidinyl, pyrrolidinyl or morpholinyl, the alkyl portions of which contain 1–6 carbon atoms; or $R^4$ is aryl or aryl substituted one or more times by alkyl, hydroxy, alkoxy, amino, alkylamino, or dialkylamino, the alkyl portions of which contain 1–6 carbon atoms;

$R^5$ and $R^6$, which may be the same or different are independently H; or a halogen; or an alkyl having 1–6 carbons; or —$OR^8$, —$SR^8$, —$(NR^8R^9)$; where $R^8$ and $R^9$, which can be the same or different, are independently H; or alkyl groups having 1–6 carbons; or $R^8$ and $R^9$ taken in combination are —$(CH_2)_4$— or —$(CH_2)_4$— or —$(CH_2)_5$— to give a 5 or 6 membered ring;

or $R^5$ and $R^6$, taken in combination are —$(CH_2)_4$— where v=3 or 4, or $R^5$ and $R^6$ form a fused aromatic ring according to formula Q2; and $R^{11}$, $R^{12}$, $R^{13}$, and $R^{14}$, which may be the same or different, are independently H; or a halogen; or an alkyl having 1–6 carbons; or —OH, —$OR^8$, —$SR^8$, or —$(NR^8R^9)$.

9. A fluorescent complex, as claimed in claim 8, wherein said nucleic acid is in a cell.

10. A fluorescent complex, as claimed in claim 8, wherein X is O or S and n=0 or 1.

11. A fluorescent complex, as claimed in claim 10, wherein each $R^1$ is H, and $R^2$ is ethyl or methyl.

12. A fluorescent complex, as claimed in claim 11, wherein said nucleic acid is in a cell.

13. A fluorescent complex, as claimed in claim 11, wherein $R^4$ is H, methyl or ethyl and $R^5$ and $R^6$ taken in combination form a fused aromatic ring according to formula Q2.

14. A fluorescent complex, as claimed in claim 13, wherein said nucleic acid polymer is single-stranded or double-stranded DNA.

15. A fluorescent complex, as claimed in claim 13, wherein said nucleic acid polymer is RNA.

16. A fluorescent complex, as claimed in claim 11, wherein $R^4$ is a substituted or unsubstituted alkylthio, alkylamino or dialkylamino.

17. A fluorescent complex, as claimed in claim 16, wherein said nucleic acid polymer is single-stranded or double-stranded DNA.

18. A fluorescent complex, as claimed in claim 16, wherein said nucleic acid polymer is RNA.

19. A method of staining nucleic acids, comprising:

a) combining a sample that contains or is thought to contain nucleic acids with a mixture containing a compound of the formula

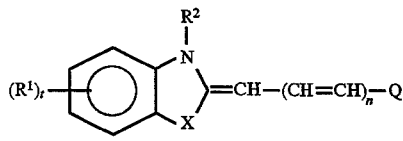

wherein each $R^1$ is independently H; or an alkyl group having from 1–6 carbons; an alkoxy group having from 1–6 carbons; or a trifluoromethyl; or a halogen; and t=1–4;

$R^2$ is an alkyl group having 1–6 carbons;

X is O, S, Se or $C(CH_3)_2$;

n=0, 1 or 2;

Q has the formula Q1 or Q2

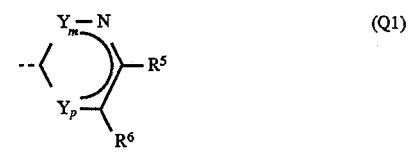

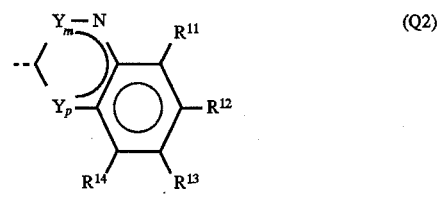

wherein

Y is —CH=$CR^4$—;

p and m=0 or 1, such that p+m=1;

$R^4$ is optionally H, alkyl, alkoxy, alkylthio, amino, monoalkylamino, dialkylamino, arylthio, aryloxy, arylamino, piperazinyl, piperidinyl, pyrrolidinyl or morpholinyl; where each alkyl group independently contains 1–6 carbons and is optionally further substituted one or more times by hydroxy, carboxy, alkoxy, alkylthio, amino, monoalkylamino, dialkylamino, trialkylammonium, piperazinyl, piperidinyl, pyrrolidinyl or morpholinyl, the alkyl portions of which contain 1–6 carbon atoms; or $R^4$ is aryl or aryl substituted one or more times by alkyl, hydroxy, alkoxy, amino, alkylamino, or dialkylamino, the alkyl portions of which contain 1–6 carbon atoms;

$R^5$ and $R^6$, which may be the same or different, are independently H; or a halogen; or an alkyl having 1–6 carbons; or —$OR^8$, —$SR^8$, —$(NR^8R^9)$; where $R^8$ and $R^9$, which can be the same or different, are independently H; or alkyl groups having 1–6 carbons; or $R^8$ and $R^9$ taken in combination are —$(CH_2)_4$— or —$(CH_2)_5$— to give a 5 or 6 membered ring;

or $R^5$ and $R^6$, taken in combination are —$(CH_2)_v$— where v=3 or 4, or $R^5$ and $R^6$ form a fused aromatic ring according to formula Q2; and $R^{11}$, $R^{12}$, $R^{13}$, and $R^{14}$, which may be the same or different, are independently H; or a halogen; or an alkyl having 1–6 carbons; or —OH, —$OR^8$, —$SR^8$, or —$(NR^8R^9)$; and b) incubating the sample and mixture for a time sufficient for said compound to combine with the nucleic acid in the sample to form one or more dye-nucleic acid complexes that give a detectable fluorescent signal;

c) observing the detectable fluorescent signal of the dye-nucleic acid complex.

20. The method of claim 19, wherein said sample comprises cells.

21. The method of claim 20, further comprising adding an additional reagent to said sample.

22. The method of claim 20, wherein said cells are blood cells.

23. The method of claim 22, wherein said compound has the formula

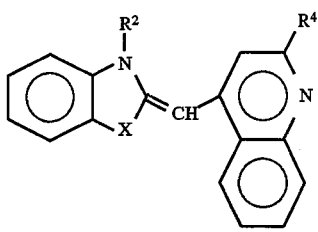

wherein

X is O or S;

R² is methyl or ethyl; and

R⁴ is H, methyl or ethyl.

24. The method of claim 20, further comprising differentiating said live cells based on said detectable fluorescent signal.

25. A kit comprising a) a compound having the formula

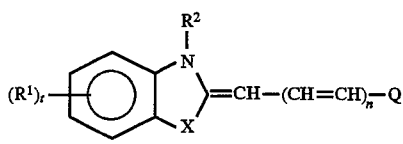

wherein each $R^1$ is independently H; or an alkyl group having from 1-6 carbons; an alkoxy group having from 1-6 carbons; or a trifluoromethyl; or a halogen; and t=1-4;

$R^2$ is an alkyl group having 1-6 carbons;

X is O, S, Se or $C(CH_3)_2$;

n=0, 1 or 2;

Q has the formula Q1 or Q2

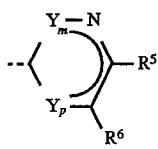

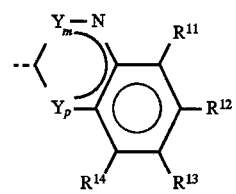

wherein

Y is $-CH=CR^4-$;

p and m=0 or 1, such that p+m=1;

$R^4$ is optionally H, alkyl, alkoxy, alkylthio, amino, monoalkylamino, dialkylamino, arylthio, aryloxy, arylamino, piperazinyl, piperidinyl, pyrrolidinyl or morpholinyl; where each alkyl group independently contains 1-6 carbons and is optionally further substituted one or more times by hydroxy, carboxy, alkoxy, alkylthio, amino, monoalkylamino, dialkylamino, trialkylammonium, piperazinyl, piperidinyl, pyrrolidinyl or morpholinyl, the alkyl portions of which contain 1-6 carbon atoms; or $R^4$ is aryl or aryl substituted one or more times by alkyl, hydroxy, alkoxy, amino, alkylamino, or dialkylamino, the alkyl portions of which contain 1-6 carbon atoms;

$R^5$ and $R^6$, which may be the same or different, are independently H; or a halogen; or an alkyl having 1-6 carbons; or $-OR^8$, $-SR^8$, $-(NR^8R^9)$; where $R^8$ and $R^9$, which can be the same or different, are independently H; or alkyl groups having 1-6 carbons; or $R^8$ and $R^9$ taken in combination are $-(CH_2)_4-$ or $-(CH_2)_5-$ to give a 5 or 6 membered ring;

or $R^5$ and $R^6$, taken in combination are $-(CH_2)_v-$ where v=3 or 4, or $R^5$ and $R^6$ form a fused aromatic ring according to formula Q2; and $R^{11}$, $R^{12}$, $R^{13}$, and $R^{14}$, which may be the same or different, are independently H; or a halogen; or an alkyl having 1-6 carbons; or $-OH$, $-OR^8$, $-SR^8$, or $-(NR^8R^9)$; and b) instructions to practice the method of claim 19.

* * * * *

UNITED STATES PATENT AND TRADEMARK OFFICE
CERTIFICATE OF CORRECTION

PATENT NO. : 5,656,449
DATED : August 12, 1997
INVENTOR(S) : Yue

It is certified that error appears in the above-indentified patent and that said Letters Patent is hereby corrected as shown below:

column 6, line 20 "office" should be --of free--.

column 13, line 19 "organcelles" should be --organelles--.

column 15, lines 32, 33, and 40 each appearance of "tie" should be --the--.

column 16, line 61 "6-methoxyquinaldine" should be --quinaldine--.

column 19, line 14 "erode" should be --crude--.

column 19, line 18 "healing" should be --heating--.

column 21, line 33 "Filly" should be --Fifty--.

column 25, line 17 "—$(CH_2)_4$—" should be -- —$(CH_2)_v$— --.

Signed and Sealed this

Fourteenth Day of July, 1998

Attest:

BRUCE LEHMAN

*Attesting Officer*     *Commissioner of Patents and Trademarks*